US00PP08776P

United States Patent [19]

van Diemen

[11] Patent Number: Plant 8,776

[45] Date of Patent: Jun. 7, 1994

[54] *FICUS MACLELLANDII* PLANT NAMED FICUS AMSTEL KING

[75] Inventor: Hubertus T. van Diemen, Aalsmeer, Netherlands

[73] Assignee: Kwekerij De Amstel, B.V., Aalsmeer, Netherlands

[21] Appl. No.: 21,358

[22] Filed: Feb. 23, 1993

[51] Int. Cl.[5] ..... A01H 5/00

[52] U.S. Cl. ..... Plt./88.9

[58] Field of Search ..... Plt. 88.9

[56] References Cited

PUBLICATIONS

Huxley, A., et al. (Eds.) "Ficus" The New Royal Horticultural Society Dictionary of Gardening vol. 2 1992, Stockton Press, N.Y. pp. 294–305.

*Primary Examiner*—James R. Feyrer

*Attorney, Agent, or Firm*—Christie, Parker & Hale

[57] ABSTRACT

A *Ficus maclellandii* plant that has wide leaves and is tolerant of stress conditions and has rapid growth habit.

1 Drawing Sheet

BACKGROUND OF THE INVENTION

The present invention comprises a new and distinct cultivar of the *Ficus maclellandii*. The varietal denomination of the new cultivar is Ficus 'Amstel King'.

The new variety was discovered as a mutation in a controlled planting of *Ficus maclellandii* in a greenhouse in Aalsmeer, The Netherlands. The mutation did not result from tissue culture but was isolated in a glass house as a discovered mutation.

SUMMARY OF THE INVENTION

The new variety is a mutation of the variety *Ficus maclellandii* and differs significantly in appearance from its parent. The leaves of the new variety are wider and somewhat longer than the parent. In addition, the growth rate of the new variety is at least 30% faster than its parent and the apical growth displays red coloration which is ever-present due to the fast metabolism of the plant even under low light and cool temperature conditions. However, from a visual standpoint the most significant distinctive feature from its parent is the larger size of the leaves.

Although the most unique feature of the new variety is the size of the leaves, its rapid growth habit and tolerance of conditions of stress make Ficus 'Amstel King' a desirable cultivar for the horticulture industry.

The new variety has been asexually reproduced vegetatively by rooted cuttings in Aalsmeer, The Netherlands. Asexual reproduction through succeeding generations has established that the combination of characteristics as herein disclosed for the new cultivar is firmly fixed and is retained through successive generations of asexual reproduction.

Comparison of Ficus 'Amstel King' With its Parent *Ficus maclellandii*

The size of the leaves of the new variety is about 4 to 5 cm across at the widest point, with an average overall length of about 22 cm. The width of the leaves of the parent variety is about 2 to 2.5 cm and the overall length is about 17 cm. Also, Ficus 'Amstel King' has a faster rate of growth, generally at least 30% greater under similar conditions, than its parent.

For a rooted cutting of 10 cm to reach a height of 1 meter for the 'Amstel King' variety will take approximately 24 weeks.

For a rooted cutting of *Ficus maclellandii* to reach a height of 1 meter from a 10 cm cutting will take approximately 36 weeks.

BRIEF DESCRIPTION OF THE ILLUSTRATION

The accompanying illustration shows a specimen of the new cultivar in a photo illustration as true to color as is reasonably possible to make in an illustration of this character.

DESCRIPTION OF THE NEW VARIETY

Ficus 'Amstel King' has not been observed under all possible environmental conditions. The phenotypic expression may vary with variations in environment such as temperature, light intensity and day length.

The following observations and descriptions are of plants grown in Aalsmeer, The Netherlands, in a greenhouse during the month of January. In this description, color references Royal Horticultural Society Colour Chart (RHSCC). The terminology used in the color descriptions herein refers to plate numbers in this color chart.

Classification:

*Botanical.*—*Ficus maclellandii* cv. Ficus 'Amstel King'.

Parentage: Mutation of *Ficus maclellandii*.

Propagation: By vegetative cuttings and other known asexual reproduction techniques.

PLANT

A. Form: Upright, multiple-branching woody ornamental.

B. Growth: Extremely vigorous with uniform branching.

*Height attained.*—About 5 meters.

C. Foliage:

1. *Size.*—About 4 to 5 cm across at widest point with average overall length about 22 cm.
2. *Quantity.*—Multiple, numerous.
3. *Color.*—New Foliage: Upper and under sides — near 144A. Old Foliage: Upper side — near 139A. Developing Foliage: Near 137A.

4. *Shape.*—Lanceolate with acuminate leaf tip.
5. *Texture.*—Smooth and glabrous, very crisp
6. *Veination.*—Single and pronounced; a single pronounced vein runs from the center of the petiole to the tip of the lance, smooth in shape and texture.
7. *Form.*—Lanceolate.
8. *Margin.*—Smooth edge.
9. *Petioles.*—About 2.5 cm and alternating.
10. *Resistance to disease.*—Resistant to disease and very resistant to leaf drop under low light and other stressful conditions; hardy.
11. *Variegation: None*

D. Wood:

*Color.*—Near 165A with striations of near 165D; new shoots are greenish brown; old wood is dark brown with almond-colored striations and specules.

E. Fruit: The new variety has not yet borne fruit or flowers under the controlled environment of the glass houses in the Netherlands in which plants have been propagated and grown.

GENERAL

Temperature range: To 1° C.; will withstand 1° C. to 35° C.

Internode spacing: About 2.5 cm.

Preferred growing conditions: 20° C. to 32° C.

Growth habit: Vigorous upright woody, multiple branching.

Leaves per stem: Multiple, alternating.

I claim:

1. A new and distinct cultivar of *Ficus maclellandii* named Ficus 'Amstel King', substantially as illustrated and described.

* * * * *

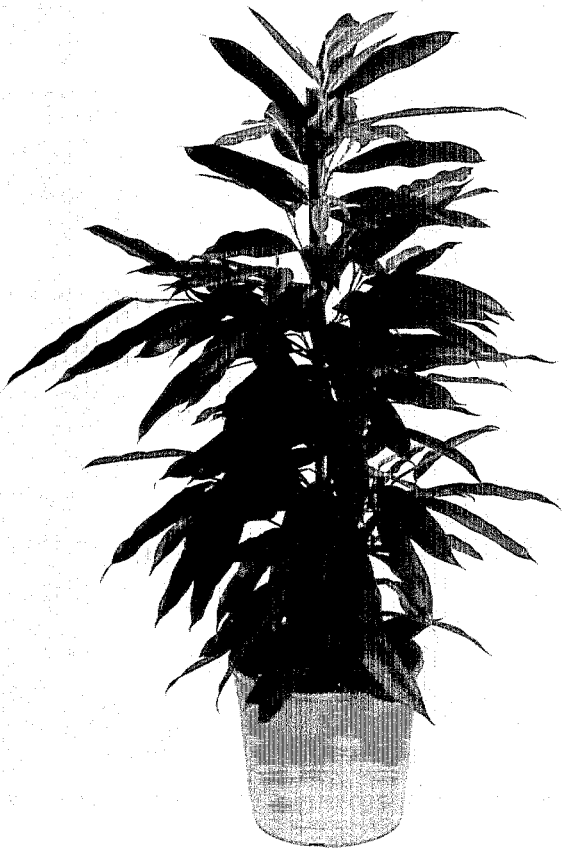

UNITED STATES PATENT AND TRADEMARK OFFICE

CERTIFICATE OF CORRECTION

PATENT NO. : Plant 8,776

DATED : June 7, 1994

INVENTOR(S) : Hubertus T. van Diemen

It is certified that error appears in the above-indentified patent and that said Letters Patent is hereby corrected as shown below:

On the Title Page, item:

[21] Application No., change "21,358" to -- 21,355 --.

Signed and Sealed this

Eighteenth Day of October, 1994

*Attest:*

Bruce Lehman

BRUCE LEHMAN

*Attesting Officer*

*Commissioner of Patents and Trademarks*